US006294662B1

(12) United States Patent
Tabibzadeh

(10) Patent No.: US 6,294,662 B1
(45) Date of Patent: Sep. 25, 2001

(54) NUCLEIC ACIDS ENCODING AN ENDOMETRIAL BLEEDING ASSOCIATED FACTOR (EBAF)

(75) Inventor: Siamak Tabibzadeh, Searingtown, NY (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/342,819

(22) Filed: Jun. 29, 1999

Related U.S. Application Data

(63) Continuation-in-part of application No. 08/919,421, filed on Aug. 27, 1997, now Pat. No. 5,916,751.
(60) Provisional application No. 60/025,800, filed on Aug. 27, 1996.

(51) Int. Cl.[7] .............................. C07H 21/04; C12Q 1/68
(52) U.S. Cl. ................... 536/23.5; 536/23.1; 536/24.31; 536/24.33; 435/6
(58) Field of Search ............................ 435/6, 7.1, 320.1; 536/23.5, 24.31, 24.33, 23.1

(56) References Cited

U.S. PATENT DOCUMENTS 6,027,917 * 2/2000 Celeste et al. ...................... 435/69.1

OTHER PUBLICATIONS

Kothapalli. Journal of Clinical Investigation. 99:2342–2350, May 1997.*

Tabibzadeh et al. Frontiers in Bioscience. 2:18–25, Jul. 1997.*

Hillier et al. GenBank Accession No. R37562, May 1995.*

Frigerio et al. GenBank Accession No. T25016, May 1997.*

* cited by examiner

*Primary Examiner*—Carla J. Myers
(74) *Attorney, Agent, or Firm*—Kohn & Associates

(57) ABSTRACT

A method for the early diagnosing of selected adenocarcinomas in a human comprising the steps of removing a bodily sample from the human, and assaying the bodily sample for elevated expression of a specific gene. The gene being assayed for in the bodily sample is the TGFB-4 gene (hereinafter referred to as the endometrial bleeding associated factor (ebaf) gene. The bodily sample can be tissue from a specific organ in the body, or a blood sample. Increased levels of ebaf in the sample relative to basal levels may be indicative of a mucinous adenocarcinoma of the colon or ovaries, or an adenocarcinoma of the testis.

7 Claims, 3 Drawing Sheets

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 1962 base pairs
      (B) TYPE: nucleic acid
      (C) STRANDEDNESS: single
      (D) TOPOLOGY: linear (iii) HYPOTHETICAL: NO (iv) ANTI-SENSE: NO (vi) ORIGINAL SOURCE:
      (A) ORGANISM: Homo sapiens (vii) IMMEDIATE SOURCE:
      (A) LIBRARY: genomic (xi) SEQUENCE DESCRIPTION: SEQ ID NO: 1:

```
CCCCACTCTG CCTCCTGCTC CCCCAGGGCA GCACCATGTG GCCCCTGTGG CTCTGCTGGG      60

CACTCTGGGT GCTGCCCCTG GCTGGCCCCG GGGCGGCCCT GACCGAGGAG CAGCTCCTGG     120

CGAGCCTGCT GCGGCAGCTG CAGCTCAGCG AGGTGCCCGT ACTGGACAGG GCCGACATGG     180

AGAAGCTGGT CATCCCCGCC CACGTGAGGG CCCAGTATGT AGTCCTGCTG CGGCGCGACG     240

GGGACCGCTC CCGCGGAAAG AGGTTCAGCC AGAGCTTCCG AGAGGTGGCC GGCAGGTTCC     300

TGGCGTCGGA GGCCAGCACA CACCTGCTGG TGTTCGGCAT GGAGCAGCGG CTGCCGCCCA     360

ACAGCGAGCT GGTGCAGGCC GTGCTGCGGC TCTTCCAGGA GCCGGTTCCC CAAGGCGCGC     420

TGCACAGGCA CGGGCGGCTG TCCCCGGCAG CGCCCAAGGC CCGGGTGACC GTCGAGTGGC     480

TGGTCCGCGA CGACGGCTCC AACCGCACCT CCCTCATCGA CTCCAGGCTG GTGTCCGTCC     540

ACGAGAGCGG CTGGAAGGCC TTCGACGTGA CCGAGGCCGT GAACTTCTGG CAGCAGCTGA     600

GCCGGCCCCC GGAGCCGCTG CTCGTACAGG TGTCGGTGCA GAGGGAGCAT CTGGGCCCGC     660

TGGCGTCCGG CGCCCACAAG CTGGTCCGCT TTGCCTCGCA GGGGGCGCCA GCCGGGCTTG     720

GGGAGCCCCA GCTGGAGCTG CACACCCTGG ACCTCAGGGA CTATGGAGCT CAGGGCGACT     780

GTGACCCTGA AGCACCAATG ACCGAGGGCA CCCGCTGCTG CCGCCAGGAG ATGTACATTG     840

ACCTGCAGGG GATGAAGTGG GCCAAGAACT GGGTGCTGGA GCCCCGGGC TTCCTGGCTT     900
```

-continued

```
ACGAGTGTGT GGGCACCTGC CAGCAGCCCC CGGAAGCCCT GGCCTTCAAT TGGCCATTTC      960
TGGGGCCGCG ACAGTGTATC GCCTCGGAGA CTGCCTCGCT GCCCATGATC GTCAGCATCA     1020
AGGAGGGAGG CAGGACCAGG CCCCAGGTGG TCAGCCTGCC AACATGAGG  GTGCAGAAGT     1080
GCAGCTGTGC CTCGGATGGG GCGCTCGTGC CAAGGAGGCT CCAGCATAGG CCCTGGTGTA     1140
TCCATTGAGC CTCTAACTGA ACGTGTGCAT AAGAGGTGGT CTTAATGTAG GGCGTTAACT     1200
TTATACTTAG CAAGTTACTC CATCCCAATT TAGTGCTCCT GTGTGACCTC GCCCTGTGTC     1260
CTTCCATTCC TGTCTTTCCC GTCCATCACC CATCCTAAGC ACTTACGTGA GTAAATAATG     1320
CAGCTCAGAT GCTGAGCTCT AGTAGGAAAT GCTGGCATGC TGATTACAAG ATACAGCTGA     1380
GCAATGCACA CATTTTCAGC TGGGAGTTTC TGTTCTCTGG CAAATTCTTC ACTGAGTCTG     1440
GAACAATAAT ACCCTATGAT TAGAACTGGG GAAACAGAAC TGAATTGCTG TGTTATATGA     1500
GGAATTAAAA CCTTCAAATC TCTATTTCCC CCAAATACTG ACCCATTCTG GACTTTTGTA     1560
AACATACCTA GGCCCCTGTT CCCCTGAGAG GGTGCTAAGA GGAAGGATGA GGGCTTCAGG     1620
CTGGGGGCAG TGGACAGGGA ATTGGGATAC CTGGATTCTG GTTCTGACAG GGCCACAAGC     1680
TAGGATCTCT AACAAACGCA GAAGGCTTTG GCTCGTCATT TCCTCTTAAA AAAGGAGGAG     1740
CTGGGCTTCA GCTCTAAGAA CTTCATTGCC CTGGGGATCA GACAGCCCCT ACCTACCCCT     1800
GCCCACTCCT CTGGAGACTG AGCCTTGCCC GTGCATATTT AGGTCATTTC CCACACTGTC     1860
TTAGAGAACT TGTCACCAGA AACCACATGT ATTTGCATGT TTTTTGTTAA TTTAGCTAAA     1920
GCAATTGAAT GTAGATACTC AGAAGAAATA AAAAATGATG TT                        1962
```

NUCLEIC ACIDS ENCODING AN ENDOMETRIAL BLEEDING ASSOCIATED FACTOR (EBAF)

CROSS REFERENCE

This application is a continuation in part of Ser. No. 08/919,421, filed Aug. 27, 1997 now U.S. Pat. No. 5,916, 751; which claims the benefit of provisional application Ser. No. 60/025,800, filed Aug. 27, 1996, incorporated herein by reference.

GOVERNMENT SUPPORT

This invention was made with Government support under Grant Number CA46866 awarded by the National Institutes of Health (NIH). The Government has certain rights in the invention.

FIELD OF INVENTION

A method for diagnosis of human bodily conditions, and more particularly, a method for diagnosing selected mucinous adenocarcinoma of the colon, or ovaries, or an adenocarcinoma of the testis.

BACKGROUND OF INVENTION

Early diagnosis of particular pathological conditions of the human body can provide patients with adequate time to make well informed decisions regarding the treatment of their pathological condition, as well as prepare for the potential incapacitation of the patient. One such pathological condition is colon cancer. The American Chemical Society has reported that colon cancer is the second most common cause of cancer in the United States (Fleischer, D. et al. *Detection and Survival of Colorectal Cancer* (1989) JAMA 261(4):580. It has been estimated that approximately 145,000 new cases of colon cancer are reported yearly in the United States, and the overall mortality rate of this pathological condition is almost 60%. Moreover, a diagnosis of colon cancer has been estimated to shorten that patient's life by six to seven years (Id). Consequently, early detection of this pathological condition offers a patient the best hope of survival.

Approximately three principal screening tests for the early detection of colon cancer or precancerous polyps are presently available to physicians. One such test is the Fecal Occult Blood Test (FOBT). Basically, this test is designed to test whether blood is present in the fecal material of the patient. Hence, this effectiveness of this test is dependent upon the assumptions that blood in the fecal material is indicative of the presence of colonic neoplasms, and that these neoplasms will bleed in sufficient quantity in order to cause a positive FOBT result.

However, it is because of these necessary assumptions that applicants believe the FOBT contains significant shortcomings as a screening tool for colon cancer. For instance, it has been shown that not all colonic neoplasms bleed sufficiently into the colon. As a result, this test is readily capable of giving false negative results.

In addition, there are other factors which could result in a false positive result for this test. For example, it has been found that aspirin and other non-inflammatory analgesics have been known to cause irritation in the stomach and increased gastro-intestinal tract blood loss, thereby producing in a false positive result. The patient's ingestion of rare beef and fruits and vegetables which contain catalases and peroxidases within 24 hours of administering the test may also cause a false positive result.

Another screening test that is available is the Carcinoembryonic Antigen (CEA) test. CEA is a glycoprotein that may be produced by cancerous lesions in the colon. This test is designed to measure the concentration of CEA in the patient's blood to determine if it is elevated relative to normal levels. It is believed that an elevated level is due directly to the presence of colon cancer in the patient. Hence it was hoped CEA would act as a genetic marker for colon cancer. Immunological techniques are usually used to measure CEA levels in the blood.

However, soon after this test became available to health professionals, it was observed that this test was simply too insensitive to recognize numerous types of colon cancers. As a result, the CEA test was relegated to the detection of a recurrence of colon cancer after surgery is performed to remove cancerous lesions from the colon. Even in this role though, it has met with only limited success. In 1993, a study on the effectiveness of CEA testing in 1017 patients was published in the Journal of the American Medical Association. The study showed that 417 patients out of the original group developed recurrent colon cancer, and 247 of these had elevated CEA levels prior to diagnosis of recurrence. However, of the remaining 600 patients, 98 also had elevated CEA levels. Hence the rate of false negatives for the test was 41%, and the rate of false-positive results was 16%. (Moertel, C., et al. *An Evaluation of the Carcinoembryonic Antigen (CEA) Test for monitoring Patients with resected Colon Cancer.* JAMA 270(8):954 (1993).

In concluding their study, the authors questioned the efficacy of the CEA Test. In support of this conclusion, they explained that, based on their data, the maximum anticipated gain from CEA monitoring would probably be a small number of lives saved (less than 1% of patients monitored) after resection and hepatic metastasis. In addition, the authors specifically stated, "Since the most defensible objective of CEA monitoring is detection of potentially resectable hepatic metastasis, it would also seem appropriate to consider alternative strategies that might fulfill this objective in a more sensitive, specific, and cost-effective manner." (Id)

Another method used to screen for colon cancer is to have the patient undergo a periodic sigmoidoscopic examination. The use of this screening test in a particular patient is dependent upon the age of the patient and whether he or she is a member of a high-risk population. Research on this screening technique has concluded this method to be the best known screening method for colon cancer presently available (see Selby, J. *Sigmoidoscopy in the Periodic Health Examination of Asymptomatic Adults* JAMA (1989) 261(4): 595)

However, researchers have also acknowledged that this screening method contains inherent limitations. For example, the high cost for the specialized instruments required to perform this screening test, and the special training required in the operation of the instruments in order to perform the procedure safely are acknowledged. Moreover, general patient discomfort while undergoing this screening is believed to be one of the obstacles in providing mass screening for the general population. Finally, health professionals acknowledge that there is a very slight risk of perforating a patient's colon while undergoing the procedure. Consequently, applicants believe a simple, cost effective screening test for colon cancer is needed.

Another type of pathological condition, present exclusively in women, is ovarian cancer. Ovarian cancer comes from cells of the ovary that grow and divide uncontrollably. Applicants believe that statistical information on ovarian cancer indicates that approximately one woman out of every fifty-five (approximately 1.8%) will develop ovarian cancer some time in her lifetime, and it was believed that in 1996, approximately 26,000 women would be diagnosed with ovarian cancer and approximately 14,500 women would die of the disease. Moreover, 85 to 90% of women diagnosed with the condition before it spreads from the ovary are cured. However, there is only a 20 to 25% chance of living after diagnosis, if the diagnosis is made after the disease has spread beyond the ovary.

Presently, there are methods available to diagnose ovarian cancer, but such methods have inherent limitations. One such method is assaying the patient's blood for elevated levels of Cancer Antigen 125 (CA 125). It has been determined that eight out of ten women with advanced ovarian cancer, and in one out of two women with cancer localized in the ovary will have such elevated levels. However, endometriosis, pelvic inflammatory disease of the tubes and ovaries, uterine fibroids, and pregnancy can also elevate levels of CA 125 in the blood, resulting in false positives.

Another method involves screening the ovaries for a growth, surgically removing the growth, and then performing a biopsy on the growth. Screening can occur with a pelvic examination, during which the physician feels for growths on the ovary, or with special types of x-rays. If such a growth is discovered, it must be surgically removed, so that a biopsy can be performed. Another such screening method is ultrasound examination of the ovaries. However, like the pelvic examination, this method provides no definitive answer regarding the presence of cancer in the ovaries.

Another pathological condition for which early diagnosis would benefit the patient is testicular cancer. With this type of cancer, the patient develops a growth within the body of the testicle. The physician must then determine whether the growth is cancerous using presently available diagnostic procedures.

One such procedure is to perform a biopsy on the growth through the scrotum. However, such a procedure presents a problem to the patient in that it could contaminate the scrotum, which could then be a site for the development of cancer. Moreover such a biopsy could disturb the pattern of nodal metastases, and make points for subsequent surgery difficult to predict.

Another such procedure is inguinal orechiectomy, which is done through an incision made above the inguinal ligament. The testicle is then brought up through the inguinal canal and examined visually. However this procedure has limitations in that it is done surgically, like the biopsy, and is a qualitative inspection of the testes. Consequently, a false positive or false negative can result from this procedure.

Another method available for diagnosing testicular cancer is assaying the patient's blood for elevated levels of Human Chorionic Gonadotrophin, beta subunit (Beta HCG). However, this method contains inherent limitations in that it has been determined that low testosterone states, and marijuana use by the patient can produce false positives.

SUMMARY OF THE INVENTION

There is provided, in accordance with the present invention, a method for the early diagnosing of selected adenocarcinomas in a human. Applicants believe that this method is accurate, dependable, inexpensive, and does not possess the shortcomings of the prior art as explained above. In particular, the present invention describes a method for diagnosing an adenocarcinoma in a human comprising the steps of removing a bodily sample from the human, and assaying the bodily sample for elevated expression of a specific gene. The bodily sample can be either tissue from a particular organ, such as the colon or the ovary, or a sample of blood. For purposes of this application, "expression" means either the transcription of the specific gene into at least one mRNA transcript, or the translation of at least one mRNA into a protein.

The specific gene referred to above is the TGFB-4 gene (hereinafter referred to as the endometrial bleeding associated factor (ebaf) gene). Applicants recently discovered this gene in humans (please see Ravi Kothapalli, Ibrahim Buyuksal, Shi-Qi Wu, Nasser Chegini, Siamak Tabibzadeh: Detection of ebaf, a novel human gene of the TGF-? superfamily; association of gene expression with endometrial bleeding J. Clin. Invest. 1997, 99:2342–2350, which is hereby incorporated by reference herein). The cDNA sequence of the ebaf gene is set forth in SEQ. ID NO. 1.

Applicants have also discovered that, due to alternative splicing during the transcription of the gene into mRNA, three different mRNA transcripts can result from the transcription of the ebaf gene. One of the transcripts is 1.5 kb in size, one is 2.1 kb, and the remaining is 2.5 kb. Consequently, such processing will produce three isoforms upon translation of the transcripts. Regardless, elevated expression of the ebaf gene can be determined from elevated levels of any transcript or any isoform. Hence, one object of the present invention is to provide an accurate, reliable method for the diagnosis and detection of an adenocarcinoma of the testis, or a mucinous adenocarcinoma of the colon in a human male.

Another object of the present invention is to provide an accurate, reliable method for the diagnosis and detection of a mucinous adenocarcinoma of the ovaries, or a mucinous adenocarcinoma of the colon in a human female.

Yet another object of the present invention is to provide a method of diagnosing and detecting a mucinous adenocarcinoma of the ovaries or colon in a female human, or a mucinous adenocarcinoma of the colon or an adenocarcinoma of the testis in a human male that is selective for such adenocarcinomas. While the ebaf gene disclosed in the present is expressed in the adenocarcinomas mentioned above, it is not expressed in other types of adenocarcinomas, such as Squamous Cell Carcinoma (SCC), lymphoma or adenocarcinoma. Consequently, the present invention is very selective for the type of adenocarcinomas it is designed to detect. Moreover, in normal tissues, the ebaf gene is expressed only the ovary, pancreas, rectum, endometrium immediately prior to and during the menstrual cycle, and weakly in the colon and the kidney. Consequently, the number of false positive resulting from the use of the present invention is limited.

Yet still another object of the present invention is to provide a blood test for adenocarcinomas of the testis, and mucinous adenocarcinomas of the colon and ovaries. As stated above, only 6 organs are presently known to express the ebaf gene constitutively. Applicants believe this constitutive expression results in a basal level of expression of the ebaf gene in the blood. However, if increased levels of expression of the ebaf gene are detected in the blood of a human relative to the basal level, they indicate the presence of an adenocarcinoma of the testis, or a mucinous adenocarcinoma of the colon or ovary. For example, if increased levels of expression of the ebaf gene are detected in a blood sample from a human male, such levels are indicative of an adenocarcinoma of the testis or a mucinous adenocarcinoma of the colon. If increased levels of expression of the ebaf gene are detected in a sample of blood taken from a female after her period, then such increased levels may be indicative of the presence of a mucinous adenocarcinoma in the colon or ovaries, provided the female does not suffer from abnormal uterine bleeding.

DESCRIPTION OF EXAMPLES OF THE INVENTION

Figure 1:
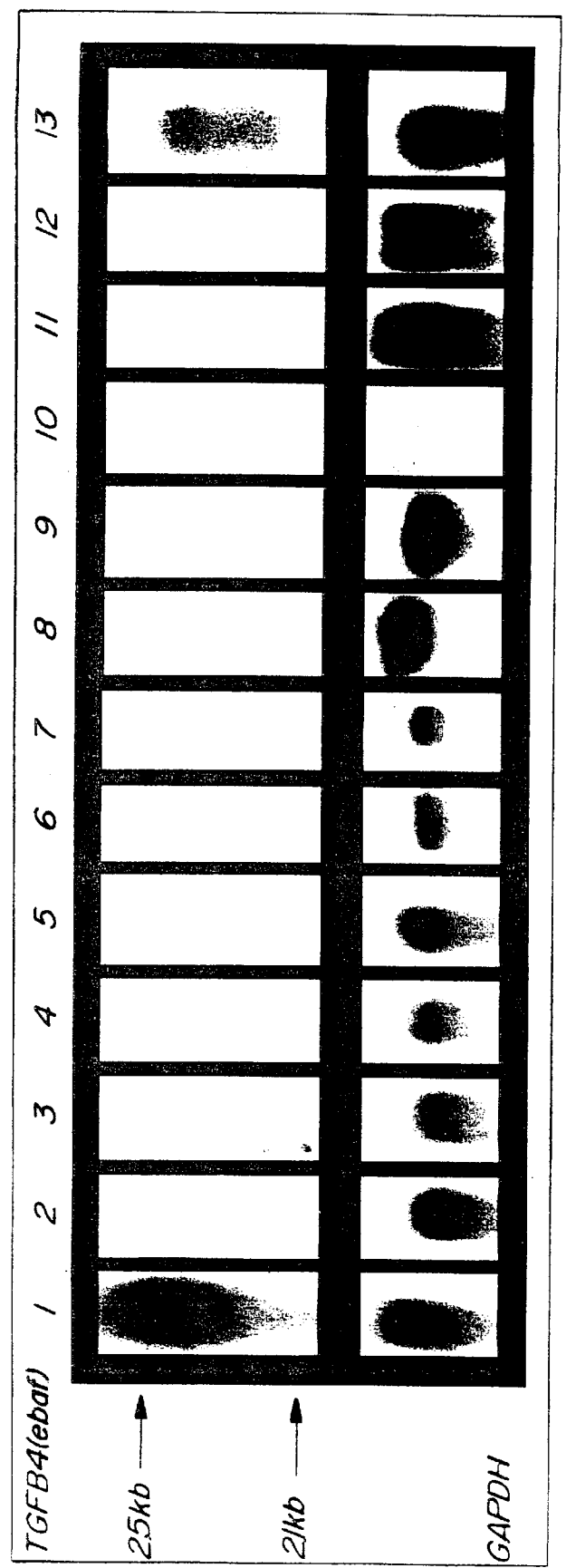
FIG. 1 is a Northern blot analysis of ebaf mRNA in normal tissues.

In the description of examples of the invention, applicants principally used the Northern Blot method to determine the expression of the ebaf gene in a particular bodily samples made up of tissues from different organs. However, as stated above, any known method capable of detecting whether levels of expression of the ebaf gene in a bodily sample are elevated relative to levels observed in a normal bodily sample of the same type is an acceptable method of practicing the invention. Such assays include, but are not limited to:

- collecting proteins from a bodily sample and performing an immunoassay on the proteins using monoclonal or polyclonal antibodies raised against the isoforms produced from the expression of the ebaf gene;
- collecting DNA from a bodily sample and performing a southern blot on the DNA using a probe that is complimentary to all or a portion of the ebaf cDNA;
- collecting RNA from a bodily sample, reverse transcribing the RNA into DNA (RT), amplifying the DNA (via PCR), and then performing a southern blot on the DNA using a probe that is complimentary to all or a portion of the ebaf cDNA.

I. Northern Blotting

The RNA was extracted from samples by using acid guanidinium thiocyanate-phenol-chloroform extraction method as described in Chomczynski, P. and N. Sacchi. Single-step method of RNA isolation by acid guanidinium thiocyanate-phenol-chloroform extraction. *Anal. Biochem.* 1987, 162:156–159 which is hereby incorporated by reference herein. The tissues samples were homogenized in "RNA STAT-60" reagent. Each 50–100 mg of tissue was homogenized in 1 ml of "RNA STAT-60" reagent in a glass or Teflon Dounce homogenizer. Each homogenate was stored for 5 minutes at room temperature to permit the complete dissociation of nucleoprotein complexes. Then, 0.2 ml of chloroform was added for each ml of "RNA STAT-60" reagent used. Each sample was covered and shaken vigorously for 15 seconds and allowed to stand at room temperature for 2–3 minutes. Following centrifugation at 12,000×g for 15 minutes at 4° C., each homogenate was separated into a lower phenol/chloroform phase and an upper aqueous phase. RNA in the upper aqueous phase was transferred to fresh tubes and mixed with isopropoanol to precipitate the total RNA. After centrifugation and drying, the precipitated RNA was dissolved in diethylpyrocarbonate (DEPC)-treated water by vigorous pipetting and by a gentle heating at 55–60° C. The amount of RNA in each sample was determined spectro-photometrically and its quality was evaluated by the integrity of ribosomal RNA by electrophoresis of 20 mg of total RNA in 1% formaldehyde-agarose gel in the presence of ethidium bromide. Northern blotting was then performed. Briefly, 20 mg of total RNA of each sample was denatured at 65° C. in an RNA loading buffer, electrophoresed in 1% agarose containing 2.2 M formaldehyde gel, and blotted onto a "HYBOND" nylon membrane using a positive pressure transfer apparatus (Posiblot, Stratagene, La Jolla, Calif.). The RNA was fixed to the membrane by UV cross-linking. Using a "PRIME-A-GENE" kit, cDNA was labeled with [$^{32}$P] to a high specific activity, and purified by Nick columns. Membranes were prehybridized in 50% formamide, 10×Denhardt's solution, 4% saline sodium citrate (SSC), 0.05 M sodium pyrophosphate and 0.1 mg/ml of denatured Hering sperm DNA at 42° C. for 2–4 hr and hybridized for 16 hours at 42° C. with $10^6$ cpm/ml of heat-denatured probe in the same buffer containing 10% dextran sulfate. Then, membranes were sequentially washed three times in 4×SSC, one time in 0.5×SSC and then one time in 0.1×SSC. All washes contained 0.1% sodium dodecyl sulfate (SDS), and were done at 65° C. for 20 minutes each. The membranes were subjected to autoradiography at −70° C. with intensifying screens. The same blot was stripped and reprobed for GAPDH. To reprobe a blot, the probe was stripped from the membrane in 75% formamide, 0.1× saline sodium phosphate ETDA (SSPE), and 0.2% SDS at 50° C. for one hour.

FIG. 1 shows the Northern Blot of ebaf mRNA in normal tissues. In FIG. 1, 20 mg total RNA from each tissue (lane 1: normal menstrual endometrium serving as the positive control and normal tissues (lane 2: spleen, lane 3: lymph node, lanes 4 and 5: stomach, lane 6: lung, lane 8: liver, lane 9 and 10: ovary, lane 11: rectum, lane 12: testis, lane 13: pancreas) was subjected to the Northern blot analysis using the entire ebaf cDNA (SEQ. ID No. 1) as the probe. As shown, a band of ebaf mRNA in the size of 2.5 kilobase (kb) is detected in the endometrium. A weak 2.1 kb ebaf mRNA is detected in the ovary, rectum, and testis. In the pancreas, both the 2.1 and 2.5 kb ebaf mRNA is detected. The ebaf gene was not expressed in the breast, stomach, small bowel, colon, kidney, lung, fallopian tube, spleen and lymph node. Table 1 displays these results in tabular form:

TABLE 1

Expression of ebaf mRNA in Normal Tissues

| Tissue | Number of tissues examined | Northern blot finding |
|---|---|---|
| Breast | 5 | — |
| Stomach | 3 | — |
| Small Bowel | 1 | — |
| Colon | 11 | 2.1 kb (weak) |
| Rectum | 2 | 2.1 kb |
| Liver | 6 | — |
| Pancreas | 2 | 2.1 and 2.5 kb |
| Kidney | 1 | 2.5 (weak) |
| Lung | 1 | — |
| Fallopian Tube | 1 | — |
| Ovary | 7 | — |
| Ovary | 1 | 2.1 kb |
| Testis | 2 | 2.1 kb |
| Spleen | 1 | — |
| Lymph node | 1 | — |

—: signal not detected
*: of eleven samples tested, only one showed a strong signal. The remaining were not apparent.

The expression of the ebaf gene was then examined in cancers derived from cells of different lineages. In eleven adenocarcinomas of colon, adjacent normal colonic tissues, non-involved by the tumor were available for the study. The RNAs from the neoplastic and surrounding normal tissues were both subjected to the Northern blot analysis for the detection of the ebaf mRNA.

Applicants also examined a host of other types of cancer for the expression of the ebaf gene. Using the same Northern Blot procedure stated in each of the previous examples, applicants collected the following data regarding the expression of the ebaf gene in non-mucinous adenocarcinomas:

TABLE 2

Expression of ebaf mRNA in the Non-Mucinous Adenocarcinomas

| Tumor Type | Number of tumors examined | Northern blot finding |
|---|---|---|
| Serous Cystadenocarcinoma of ovary | 2 | 2.1 |
| Serous Cystadenocarcinoma of ovary | 2 | 2.5 |
| Serous Cystadenocarcinoma of ovary | 5 | — |
| Adenocarcinoma of the colon metastatic to ovary | 1 | — |
| Endometrioid adenocarcinoma of ovary | 1 | — |
| Non-mucinous adenocarcinoma of colon | 7 | — |
| Non-mucinous adenocarcinoma of uterine cervix | 1 | — |
| Non-mucinous adenocarcinoma of the stomach | 3 | — |
| Hepatocellular carcinoma | 3 | — |
| Renal Cell Carcinoma | 3 | — |
| Liver metastasis; Consistent with colonic Primary | 6 | — |
| Adenocarcinoma of lung | 7 | — |
| Adenocarcinoma of breast | 5 | — |

*: Normal tissues around the tumors were available for the Northern blot analysis and did not exhibit ebaf mRNA
—: Signal not detected Squamous cell carcinomas and non-epithelial tumors for the expression were also examined for expression of the ebaf gene. The same Northern Blot protocol as explained above was also used for these tumors. The results of these tests are shown in Tables 3 and 4, respectively.

TABLE 3

Expression of ebaf mRNA in Squamous Cell Carcinomas

| Tumor Type | Number of tumors examined | Northern blot finding |
|---|---|---|
| SCC of the Larynx | 1 | — |
| SCC of the Lung | 4 | — |
| SCC of the Uterine cervix | 1 | — |

—: Signal not detected

TABLE 4

Expression of ebaf mRNA in Non-epithelial Tumors

| Tumor Type | Number of tumors examined | Northern blot finding |
|---|---|---|
| Leiomyosarcoma, gastric | 1 | — |
| Leiomyosarcoma, colon | 1 | — |
| Leiomyosarcoma, pelvic | 1 | — |
| Chondrosarcoma, thoracic wall | 1 | — |
| Osteosarcoma, metastatic to the lung | 3 | — |
| Liposarcoma, retroperitoneum | 1 | — |
| Synovial sarcoma, metastatic to the chest wall | | |
| Synovial sarcoma, parotid | 1 | — |
| Synovial sarcoma, Leg | | |
| Angiosarcoma, mediastinal | 1 | — |
| Lymphoma | 1 | — |
| Lymphoma, B cell type | | |
| Lymphoma, B cell, spleen | 1 | — |
| Lymphoma, T cell, groin | 1 | — |
| Lymphoma, T cell, angiocentric, hip | 1 | — |
| Hodgkin's Disease, mixed cell type, lymph node | 1 | — |
| Melanoma | 5 | — |

—: signal not detected

EXAMPLE 1

Detection of Mucinous Adenocarcinomas of the Colon

Figure 2:
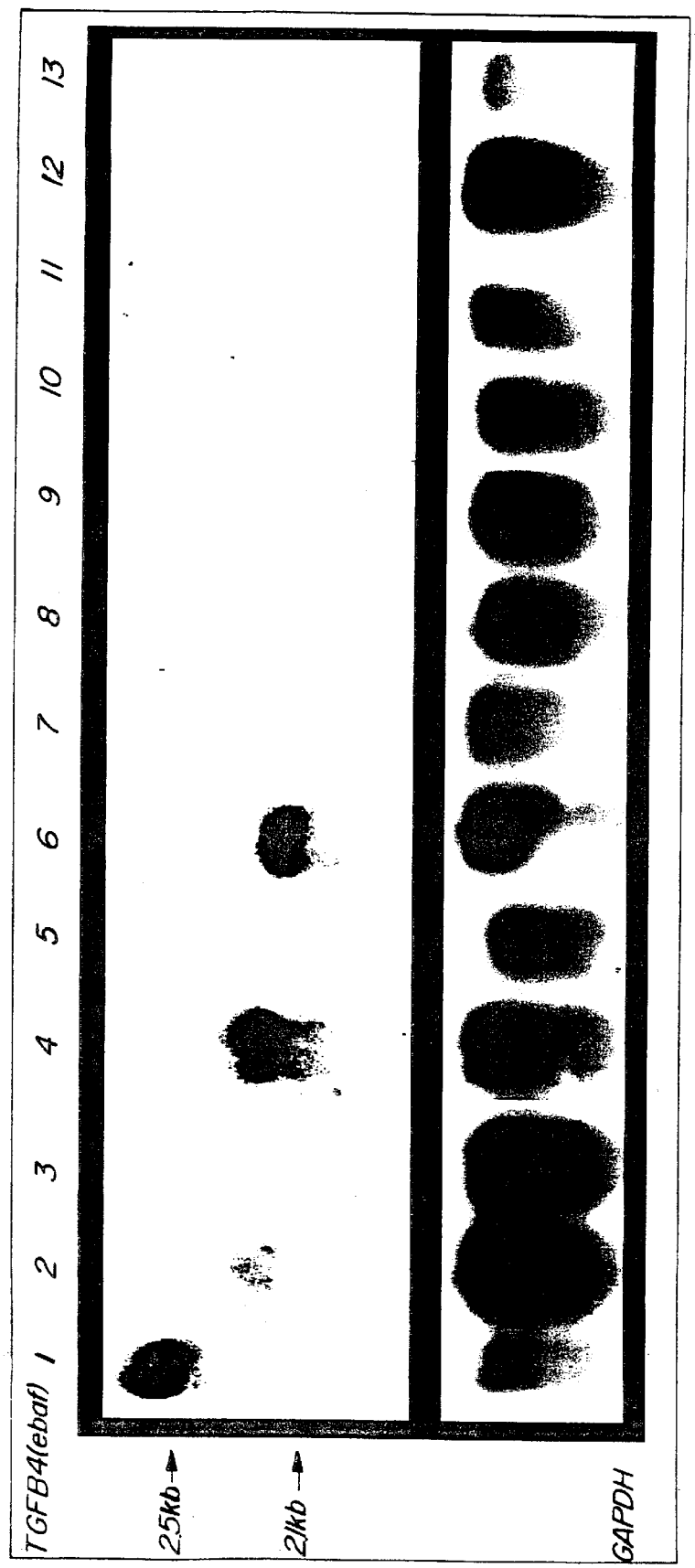
FIG. 2 is a Northern blot analysis of ebaf mRNA in colonic adenocarcinomas.

In FIG. 2, 20 mg total RNA from a normal late secretory endometrium which served as the positive control (lane 1) as well as mucinous adenocarcinomas of colon (lanes 2,4,6), non-mucinous adenocarcinomas of colon (lanes 8, 10, and 12) and adjacent normal colon (lanes 3, 5, 7, 9, 11 and 13) was subjected to the Northern blot analysis using the entire placental-derived ebaf cDNA as the probe (upper panel). Here, the expression of a 2.1 kb ebaf mRNA was detected in seven of the eleven cases of adenocarcinomas of the colon. The histological evaluation of the positive cases revealed them to have a mucinous differentiation.

EXAMPLE 2

Detection of Adenocarcinomas of the Testis

Figure 3:
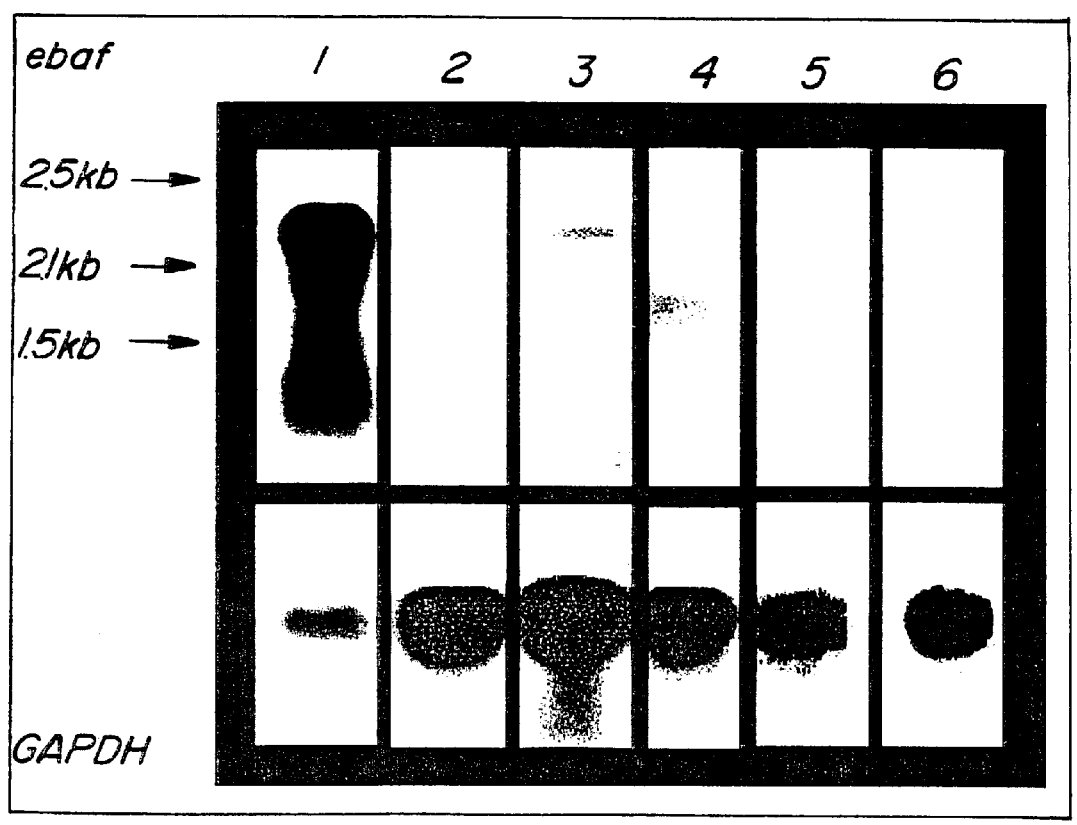
FIG. 3 is a Northern blot analysis of ebaf mRNA in testicular cancers

FIG. 3 is a Northern blot displaying the results of an examination of five cases of testicular cancer for the expression of ebaf gene. 20 mg total RNA from a normal menstrual endometrium which served as the positive control (lane 1) and each tumor tissue (lane 2: teratoma-embryonal cell carcinoma, lane 3: mixed germ cell tumor containing embryonal carcinoma, lanes 4–6; seminoma) were subjected to the Northern blot analysis using the entire placental-derived ebaf cDNA as the probe (upper panel). The blot was exposed for long duration to detect ebaf mRNA in the neoplastic tissues. This resulted in the overexpression of the ebaf mRNAs detected in the endometrium.

The results shown in FIG. 3 indicate that a 2.5 kb ebaf mRNA is detected in the tumors containing embryonal carcinoma. The 2.1 kb mRNA is also detected in two out of three cases of seminoma. The integrity of RNA and equal loading was verified by staining the 18S and 28S ribosomal RNAs (not shown) and hybridization of the blots with a cDNA probe to GAPDH (lower panel).

II. RT-PCR of RNA in the Sample Followed by Southern Blotting

Cells in the bodily sample should be lysed in 0.8 ml of "TRIREAGENT" solution (MRC Inc, Cincinnati, Ohio) in the presence of glycogen carrier. Supernatant containing RNA should be combined with 0.2 ml of chloroform, precipitated with isopropanol and washed with 70% ethanol. The RNA pellet should then be dissolved in RNAse-free water and incubated at 37° C. with 40 U DNAse I (Gibco-BRL Life Technologies) for 30 minutes. The reaction would be terminated by the addition of EDTA (20 mM) and incubation for 10 min at 65° C. Total RNA should then be precipitated overnight at −80° C. by the addition of three volumes of absolute ethanol-sodium chloride mixture. The quantity of the RNA would then be determined spectrophotometrically.

The total RNA would then be reverse transcribed in a 20 ml volume containing 2 mg RNA; 0.2 mg oligo(dT), 1.25 mM of each of dATP, dCTP, dGTP, dTTP; 5 U AMV reverse transcriptase; 10 mM MeHgOH, 88 mM β-mercaptoethanol; 10 U RNAsin; 100 mM Tris-HCl (pH 8.3); 40 mM KCl and 10 mM MgCl2. After 60 minutes of incubation at 42° C., the reaction mixture would be heated to 95° C. for 3 minutes. Following addition of 5 U of AMV, the reverse transcription would be carried out for an additional 60 minutes. After a final incubation at 95° C. for 3 minutes, reverse transcription would be terminated by placing the reaction mixture at 0° C.

1 mg of reverse transcribed RNA would then be amplified with 0.5–1 mM of each of the 5' and 3' primers specific for IL-10 in a 50 ml reaction volume containing 1.25 U Ampli-Taq DNA polymerase, 1.25 mM $MgCl_2$, 20 mM of each of dATP, dCTP, dGTP, dTTP, 10 mM Tris-HCl (pH 8.3), 50 mM KCl, and sterile distilled water. Negative control tubes would receive non-reverse transcribed RNA to verify absence of contaminating DNA. Positive control tubes would receive all the reagents in the reaction mixture, however, the primers used would be specific for β-actin. The reaction mixture would be overlayered with 50 ml of mineral oil and the tubes would be heated for 5 minutes at 95° C. After initiation of temperature cycling with a Dual-Block Thermal Cycler (Ericomp, San Diego, Calif.), samples would be amplified for 35 cycles. The denaturation temperature would be 95° C. for 1 minute, annealing temperature would be 55° C. for 1 minute and the extension temperature would be 72° C. for 2.5 minutes. Temperature cycling would be concluded with a final extension at 72° C. for 10 minutes and the reaction products would be maintained at 4° C. Amplified products will be resolved in a 2% agarose gel and the bands would be visualized by ethidium bromide staining. The fX174 Hae III RF DNA fragments and the 123 basepair DNA ladder will be used as molecular weight markers.

III. Immunoassay

Once antibodies have been raised against the ebaf isoforms, immunoassays can be used to determine whether a bodily sample exhibits increased levels of expression of the ebaf gene. Either polyclonal or monoclonal antibodies can be used in these assays. The level of expression of the ebaf gene observed from any of these assays should be compared with the basal level of expression the ebaf believed to be in present in healthy samples. If the level of expression is increased relative to this basal level, it is indicative to an adenocarcinoma of the testis, or a mucinous adenocarcinoma of the colon or ovaries.

A. Western Blotting

Initially, proteins in the bodily sample are solubilized by adding to the bodily sample an equal volume of 2×SDS lysis buffer (6% SDS, 0.14 M Tris, pH 6.8, 22.4% glycerol) and the chromosomal DNA would be sheared by repeatedly passing the sample through a 20-gauge needle and then through a 26-gauge needle. The sample would then be spun at 10,000×g for 10 minutes and the amount of protein in the supernatants would be determined using the BCA assay kit (Pierce, Rockford, Ill.). Then, mercaptoethanol (5%) and bromophenol blue (0.5%) would be added and the sample will be boiled for 5 minutes.

Tissue lysates would then be subjected to SDS-PAGE and separated proteins would be transferred to a nitrocellulose or nylon membrane. The membrane would be preblocked by incubation in TBST (10 mM Tris, pH 8.0; 150 mM NaCl; 0.05% Tween-20) containing 3% bovine serum albumin (BSA) at 25° C. for two hours. After washings in TBST (×4), the membrane would be stained by avidin-biotin-peroxidase complex (ABC) procedure (Hsu et al, 1981). This would be done by sequential incubation of the blot, with TBST containing 1% BSA and primary antibody (2–12 hours), and then with secondary antibody (2 hours), and finally ABC (2 hours). Each incubation would be carried at 37° C. and will be followed by two washes in TBST. The immunoreactive band(s) would be revealed by incubation of the blot with a mixture of 3,3' diaminobenzidine tetrahydrochloride (DAB)—$H_2O_2$. As controls, primary antibody, secondary antibody or ABC would be omitted from the staining reaction. Primary antibody would be substituted with isotype specific antibody or pre-immune serum at the same protein concentration.

B. Immunohistochemical Staining

Frozen sections will be fixed in 10% buffered formalin for 5 minutes and then washed in 0.1 M PBS. If paraffin sections are used, these will be deparaffinized in xylene and descending series of ethyl alcohol and finally washed in 0.1 M PBS.

Immunostaining would be performed according to the ABC procedure as described in the Western Blot. When paraffin sections are used, if no signal can be detected, sections would be treated prior to immunostaining with pepsin or trypsin as described (Shah et al, 1987a,b). Sections to be viewed at the light microscopic level will be evaluated with and without counterstain.

C. Enzyme Linked Immunosorbent Assay (ELISA)

ELISA is based on antigen-antibody reaction and a subsequent enzyme-mediated color development. The ELISA plates would be made in this laboratory as described in Harlow, E. and Lane, D. *Antibodies: A Laboratory Manual.* Cold Spring Harbor Laboratory, Cold Spring Harbor, N.Y. (1988). If only a monoclonal antibody is available, the antibody capture assay should be used. When both polyclonal and monoclonal antibodies are available the sandwich ELISA for detecting and quantifying the antigen should be used.

Initially, polyclonal antiserum would be raised in rabbits immunized with a bacterially produced chimeric fusion protein or a synthesized peptide of at least one of the isoforms of produced from ebaf gene expression. If required, a second peptide would be used to raise a second polyclonal antiserum or monoclonal antibody specific to a different protein domain. Monoclonal antibodies would be synthesized by a commercial vendor (bioWorld, Dublin, Ohio). The positive clones would be identified by ELISA and then expanded. The specificity of the monoclonal antibodies would be tested against the in vitro expressed proteins.

In the antibody capture assay, known amounts of purified antigen and the bodily sample with an unknown amount of antigen would be bound to the individual wells of a PVC microtitre plate. PVC will bind approximately 100 ng/well (300 ng/cm2). The plate would be incubated at room temperature for two hours. The plate would then be washed in PBS and remaining sites on the PVC plate would be saturated overnight in a humid atmosphere at room temperature with a blocking buffer (3% BSA/PBS) containing 0.2% sodium azide. After washing the plate twice with PBS, 50 ml of alkaline phosphatase-labeled antibody solution prepared in the same buffer would be added to each well and incubated for two hours at room temperature in a humid atmosphere. The unbound antibody would be removed by washing the plates four times in PBS.

To ensure that the assay is accurate, the amount of alkaline phosphatase-labeled antibody will be used in excess. The level of secondary antibody needed will be determined by titrating the alkaline phosphatase-labeled antibody. Once standards are prepared for the detection of known quantities of purified protein, the amount of protein in the samples will be determined using the kit. The amount of unknown protein will be extrapolated from a standard curve based on the known amounts of protein.

In the sandwich ELISA, the plates would be coated with the primary monoclonal antibody (20 mg/ml in PBS). After washing the wells with PBS, 50 ml of known amounts of purified antigen and various dilutions of lysate from the bodily sample would be added to the various wells of the plate. After washing, the alkaline phosphatase-labeled antibody to the antigen would be added and the plates re-washed. Each incubation would be for two hours at room temperature. A chemiluminescent detection system (Tropix, Bedfor, Mass.) would be used for detection. This system includes incubation of the plates with an antibody, followed by activation of a substrate (CSPD) that emits light. The amount of light emitted would be directly related to the level of expression of the ebaf gene in the sample lysate, and that level would be quantitated by luminometry.

Applicants believe that, any method, either known now or subsequently discovered, which is capable of determining whether the ebaf gene is being expressed in a particular bodily tissue, is an acceptable method to practice the present invention. Hence, many other variations and modifications of the invention will be apparent to those skilled in the art without departing from the spirit and scope of the invention. The above-described embodiments are, therefore, intended to be merely exemplary, and all such variations and modifications are intended to be included within the scope of the invention.

What is claimed is:

1. An isolated nucleic acid molecule encoding an endometrial bleeding associated factor (ebaf) having the nucleic acid sequence shown in SEQ ID NO. 1.
2. An isolated nucleic acid molecule of claim 1 which is a DNA molecule.
3. An isolated nucleic acid molecule of claim 1 which is a cDNA molecule.
4. An isolated nucleic acid molecule of claim 1 which is an RNA molecule.
5. A 1.5 kb mRNA transcript encoding an isoform of ebaf.
6. A 2.5 kb mRNA transcript encoding an isoform of ebaf.
7. An isolated nucleic acid molecule of claim 1 which is a probe for detecting the presence of ebaf nucleic acid in bodily samples.

* * * * *